US009217708B2

United States Patent
Yanagita et al.

(10) Patent No.: US 9,217,708 B2
(45) Date of Patent: Dec. 22, 2015

(54) EQUIPMENT AND METHOD FOR DIAGNOSING SLIDING CONDITION OF ROTATING ELECTRICAL MACHINE

(71) Applicant: Mitsubishi Hitachi Power Systems, Ltd., Yokohama, Kanagawa (JP)

(72) Inventors: Norihito Yanagita, Tokyo (JP); Tatsuro Kato, Tokyo (JP); Takeshi Iwata, Tokyo (JP)

(73) Assignee: Mitsubishi Hitachi Power Systems, Ltd., Kanagawa (JP)

( * ) Notice: Subject to any disclaimer, the term of this patent is extended or adjusted under 35 U.S.C. 154(b) by 94 days.

(21) Appl. No.: 14/065,531

(22) Filed: Oct. 29, 2013

(65) Prior Publication Data

US 2014/0118746 A1 May 1, 2014

(30) Foreign Application Priority Data

Oct. 30, 2012 (JP) ................................. 2012-238633

(51) Int. Cl.
| | |
|---|---|
| *G01N 21/55* | (2014.01) |
| *G01N 21/31* | (2006.01) |
| *G01N 21/84* | (2006.01) |
| *H02K 13/00* | (2006.01) |
| *H02K 11/00* | (2006.01) |
| *G01N 21/94* | (2006.01) |

(52) U.S. Cl.
CPC .............. *G01N 21/55* (2013.01); *G01N 21/314* (2013.01); *G01N 21/8422* (2013.01); *H02K 11/001* (2013.01); *H02K 13/00* (2013.01); *G01N 2021/8427* (2013.01); *G01N 2021/945* (2013.01); *G01N 2201/0618* (2013.01)

(58) Field of Classification Search
CPC ........................ G01N 21/00; G01N 2021/8427
USPC ............................................. 356/237.1, 237.2
See application file for complete search history.

(56) References Cited

U.S. PATENT DOCUMENTS 2,938,424 A * 5/1960 Herriott ...................... 250/222.1
4,227,809 A * 10/1980 Satoh et al. ................. 356/237.2
(Continued)

FOREIGN PATENT DOCUMENTS

| JP | 2009-222575 A | 10/2009 |
|---|---|---|
| JP | 2013-90425 A | 5/2013 |

OTHER PUBLICATIONS

European Search Report for Application No. 1319076.5, dated Jan. 31, 2014.

*Primary Examiner* — Roy M Punnoose
(74) *Attorney, Agent, or Firm* — Crowell & Moring LLP

(57) ABSTRACT

Disclosed are equipment and method for diagnosing the sliding condition of a rotating electrical machine that make it possible to achieve early detection of abnormal sliding with a simple configuration containing flexibly arranged elements and reduce the downtime and maintenance cost of the rotating electrical machine. The equipment for diagnosing the sliding condition of a rotating electrical machine includes a light source that emits light onto the sliding surface of a collecting brush relative to the surface of a rotating body of the rotating electrical machine, a light-receiving section that receives the light reflected from the sliding surface, and a determination section that processes a signal from the light-receiving section. The determination section detects an increase in a specific wavelength component of the reflected light to determine whether the sliding condition of the rotating body surface of the rotating electrical machine is abnormal.

9 Claims, 7 Drawing Sheets

(56) References Cited

U.S. PATENT DOCUMENTS

| | | | |
|---|---|---|---|
| 4,937,449 A * | 6/1990 | Kreuzer et al. | 250/351 |
| 6,580,511 B1 * | 6/2003 | Discenzo | 356/477 |
| 6,816,250 B1 * | 11/2004 | Shuster et al. | 356/237.2 |
| 6,963,076 B1 * | 11/2005 | Zaman et al. | 250/559.4 |
| 6,980,298 B2 * | 12/2005 | Discenzo | 356/477 |
| 7,551,288 B1 * | 6/2009 | Discenzo | 356/477 |
| 7,705,744 B2 * | 4/2010 | Cutsforth | 340/686.1 |
| 8,408,797 B2 * | 4/2013 | Chen et al. | 384/100 |
| 8,497,985 B2 * | 7/2013 | Hayashi et al. | 356/237.2 |
| 8,830,078 B2 * | 9/2014 | Chen et al. | 340/682 |
| 2003/0202188 A1 * | 10/2003 | Discenzso | 356/477 |
| 2008/0291040 A1 * | 11/2008 | Cutsforth | 340/653 |
| 2008/0305244 A1 * | 12/2008 | Cui et al. | 427/9 |
| 2013/0058604 A1 * | 3/2013 | Chen et al. | 384/322 |
| 2013/0183436 A1 * | 7/2013 | Chen et al. | 427/8 |

* cited by examiner

EQUIPMENT AND METHOD FOR DIAGNOSING SLIDING CONDITION OF ROTATING ELECTRICAL MACHINE

CLAIM OF PRIORITY

The present application claims priority from Japanese Patent applications serial No. 2012-238633 filed on Oct. 30, 2012, the respective contents of which are hereby incorporated by reference into this application.

FIELD OF THE INVENTION

The present invention relates to a rotating electrical machine such as a generator or electric motor with an electric sliding mechanism. More specifically, the present invention relates to equipment and method for diagnosing the sliding condition of a rotating electrical machine that are used to achieve early detection of abnormal sliding of an electric sliding mechanism represented by a slip ring and a collecting brush.

BACKGROUND OF THE INVENTION

The so-called electric sliding mechanism is a mechanism in which two different electric parts come into contact with each other and slide while conducting electricity between them. The electric sliding mechanism, which is represented by a collecting brush and a slip ring of a generator, is used in various products. It is essential that the electric sliding mechanism be inspected and replaced as needed because a relevant electric part (the collecting brush in the current example) gradually wears.

However, the electric parts variously wear depending on ambient environmental conditions and load changes so that their wear rate varies. Further, as the electric parts differ in the flow of an electric current, the wear rate may vary from one electric part to another. Therefore, if the sliding condition of each electric part is left uninspected, the electric sliding mechanism may stop functioning to cause a serious accident. If, for example, abnormal sliding occurs between the collecting brush (fixed part) and slip ring (rotary part) of the generator, the generator becomes unavailable and entails a considerable maintenance cost due, for instance, to unexpected slip ring replacement.

Meanwhile, diagnosing the surface condition of the slip ring is effective for early detection of abnormal sliding in the power generator. However, the inspection of the surface condition, such as the inspection of gloss, hue, or surface irregularities, frequently depends on the experience of maintenance personnel who conducts a visual or tactile inspection. In reality, therefore, it is practically difficult to obtain an opportunity of allowing well-experienced maintenance personnel to achieve early detection of abnormal sliding.

As such being the case, a quantitative diagnostic technology for sliding surface inspection, which is not dependent on experience, is disclosed in Japanese Unexamined Patent Application Publication No. 2009-222575. A configuration described in Japanese Unexamined Patent Application Publication No. 2009-222575 receives light reflected from the surface of a commutator of an electric motor, extracts a specular reflection component from the reflected light, and compares the glossiness of the specular reflection component with a threshold value to detect abnormal sliding.

When, for instance, the collecting brush and the slip ring slide normally, the collecting brush and the slip ring, which have a curved surface, are sliding in substantially full contact with each other. Therefore, an electric current flows uniformly over a substantially entire surface.

Meanwhile, abnormal sliding occurs when the collecting brush jumps away from the slip ring for some reason or is placed in a biased position. In this state, an overcurrent flows over a portion of the surface of the collecting brush that is sliding in contact with the slip ring. Further, a small discharge, which occurs in an open condition in which the collecting brush and the slip ring come close to each other and go away from each other, occurs frequently.

In the event of the small discharge, the material of the collecting brush scatters and attaches to the surface of the slip ring. A metal graphite brush, which is mainly used as the collecting brush, is made of a copper-graphite alloy. As copper is lower in melting point and boiling point than graphite, the electric discharge tolerance of copper is weak. Therefore, in the event of the small discharge, the copper scatters and excessively attaches to the surface of the slip ring, thereby creating a copper-rich surface film condition.

In an abnormal sliding condition, it is understood that the above phenomenon gradually develops. Meanwhile, a method described in Japanese Unexamined Patent Application Publication No. 2009-222575 uses the glossiness of specular reflected light. However, when the glossiness is to be measured, only the intensity of specular reflected light from a sliding surface is quantified without making a wavelength selection. Thus, the aforementioned hue is not examined for identification. This makes it impossible to recognize the excessive attachment of copper, which is a phenomenon concomitant to abnormal sliding.

Further, to obtain the specular reflected light, it is necessary that a light source, which emits light, and a light-receiving section, which detects reflected light, be disposed line-symmetrically with respect to the normal line of the surface of the commutator (the angle of incidence and the angle of reflection be 20 degrees or 60 degrees). In reality, however, it is difficult to achieve such a positional relationship and obtain a desired result at an actual installation site. It is more difficult to achieve such a positional relationship at an installation site near the surface of a rotating body such as the slip ring.

The present invention has been made in view of the above circumstances and provides equipment and method for diagnosing the sliding condition of a rotating electrical machine that make it possible to achieve early detection of abnormal sliding with a simple configuration containing flexibly arranged elements and reduce the downtime and maintenance cost of the rotating electrical machine.

SUMMARY OF THE INVENTION

According to an aspect of the present invention, there is provided equipment for diagnosing the sliding condition of a rotating electrical machine that includes a light source, a light-receiving section, and a determination section. Light emitted from the light source is incident on the sliding surface of a collecting brush relative to the surface of a rotating body of the rotating electrical machine. The light-receiving section receives the light reflected from the sliding surface. The determination section processes a signal from the light-receiving section. The determination section detects an increase in a specific wavelength component of the reflected light to determine whether the sliding condition of the rotating body surface of the rotating electrical machine is abnormal.

The present invention makes it possible to achieve early detection of abnormal sliding with a simple configuration containing flexibly arranged elements, minimize the possibility of sudden generator shutdown due, for instance, to an unexpected slip ring failure, and reduce the cost of maintenance performed after such a failure.

DETAILED DESCRIPTION OF THE PREFERRED EMBODIMENTS

Before embodiments of the present invention are described with reference to the accompanying drawings, a new finding obtained by the inventors of the present invention will be described. As mentioned earlier, when a small discharge occurs due to abnormal sliding, the material of a collecting brush scatters and excessively attaches to the surface of a slip ring, thereby creating, for example, a copper-rich surface film condition.

Figure 7:
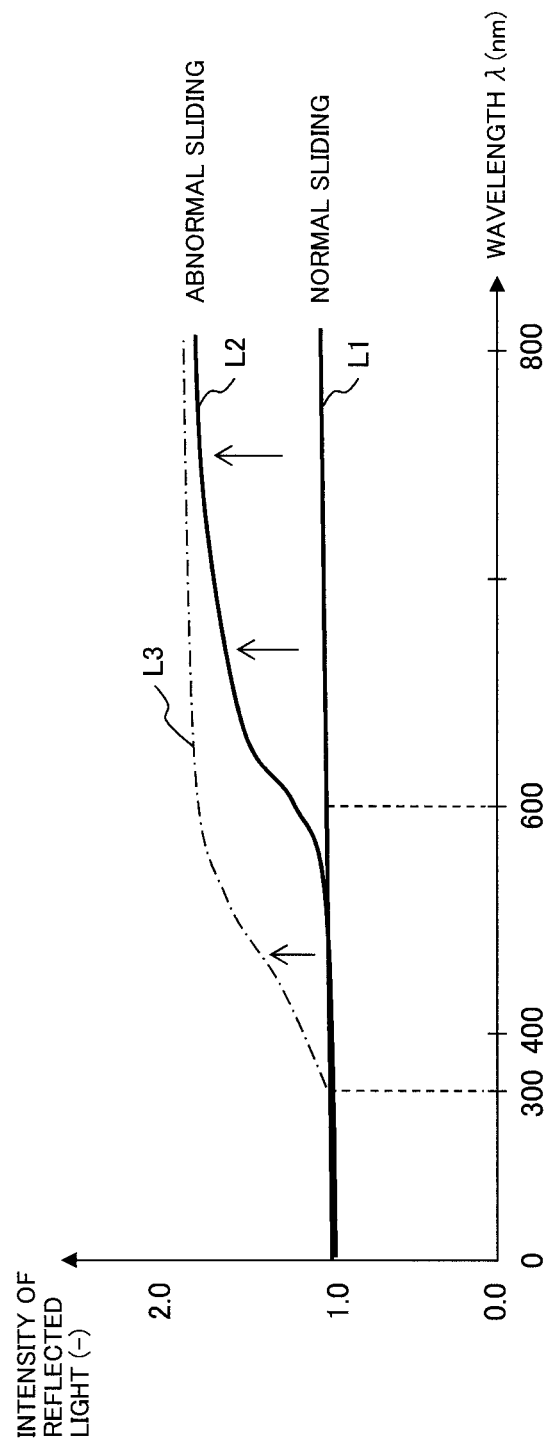
FIG. 7 is a diagram illustrating changes in a reflected light spectrum of the sliding surface of a slip ring.

The inventors of the present invention allowed a white light source to emit light on the slip ring, measured the optical spectrum of resulting reflected light, and observed such measurements for a long period of time beginning with a period of normal sliding. The result is shown in FIG. 7. In FIG. 7, the horizontal axis represents the wavelength of the optical spectrum of the reflected light, and the vertical axis represents the reflected light intensity of each wavelength. In FIG. 7, L1 is a line (straight line) indicating the reflected light intensity of each wavelength of light reflected during normal sliding. L2 and L3 indicate the reflected light intensity of each wavelength of light reflected after abnormal sliding that occurred over time.

It should be noted, however, that L2 represents characteristics obtained when copper used to form the collecting brush scattered to create a copper-rich surface film condition, and that L3 represents characteristics obtained when silver used to form the collecting brush scattered to create a silver-rich surface film condition.

From the result of the above measurements, the inventors of the present invention found that the surface intensity of reflected light increases at a wavelength of 600 nm or more when abnormal sliding occurs during the use of a collecting brush made of copper although the surface intensity of reflected light is independent of wavelength and substantially fixed during normal sliding. This phenomenon is in agreement with the characteristics of copper whose spectral reflectivity increases on the long-wavelength side of visible light (600 to 800 nm). The inventors of the present invention also found that the surface intensity of reflected light increases at a wavelength of 300 nm or more when abnormal sliding occurs during the use of a collecting brush made of silver. Although FIG. 7 does not show a wavelength region of 800 nm or more, the same tendency of increasing intensity was found in such a wavelength region.

In the description of the present invention, as regards a wavelength region depicted in relation to the characteristics shown in FIG. 7, a wavelength component of a wavelength region where the reflected light intensity increases during abnormal sliding is referred to as a specific wavelength component, whereas a wavelength component of a wavelength region where the reflected light intensity does not increase during abnormal sliding is referred to as a nonspecific wavelength component. When the collecting brush shown in FIG. 7 is made of copper, the wavelength component of a wavelength region of, for example, 600 nm or more, in which the reflected light intensity is salient, is a specific wavelength component, whereas the wavelength component of a wavelength region of less than 600 nm is a nonspecific wavelength component.

The present invention will be described with respect to some particular embodiments that utilize the above-described new finding (the intensity of reflected light having a wavelength of not less than a specific wavelength increases during abnormal sliding).

First Embodiment

Figure 1:
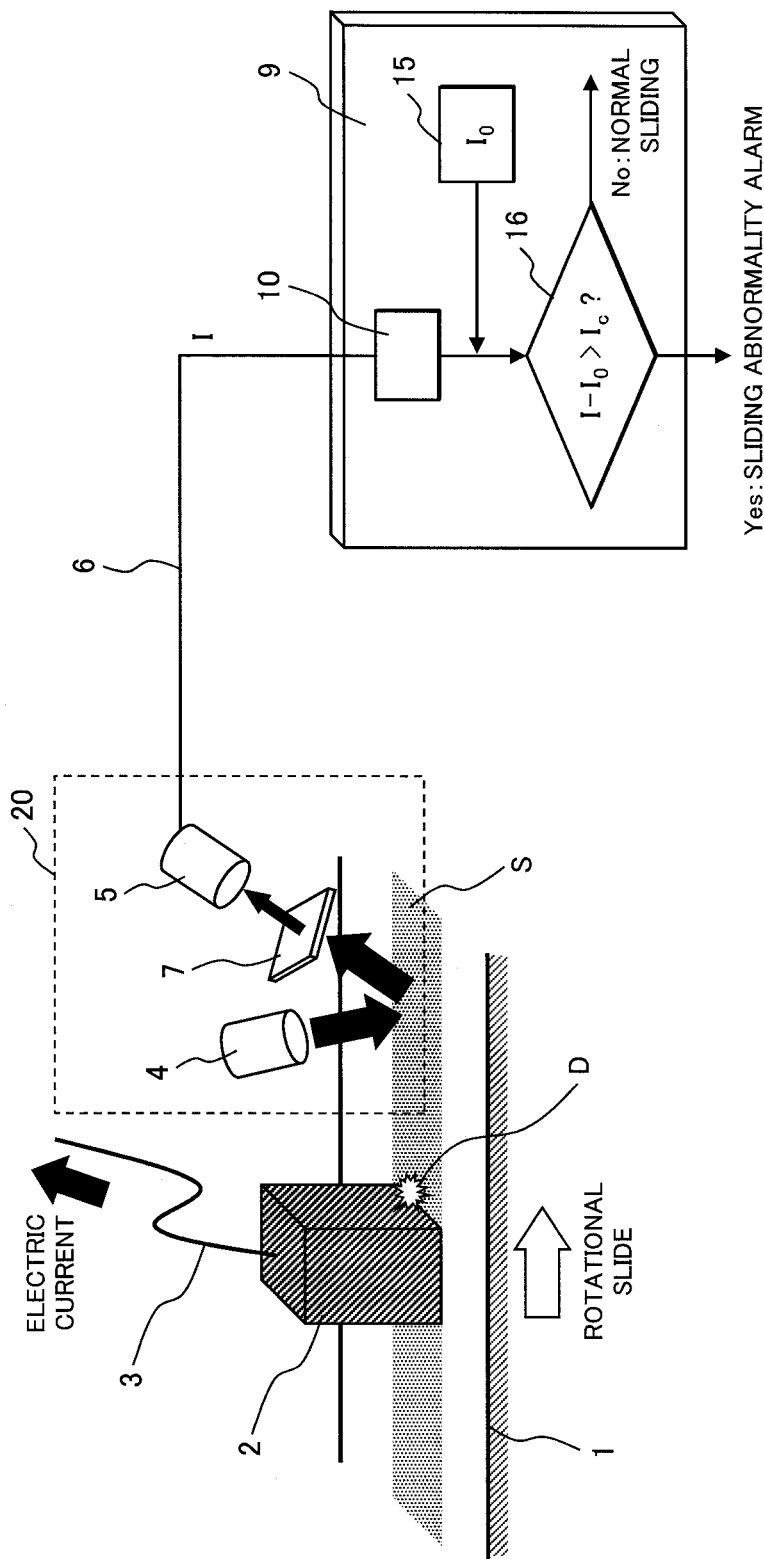
FIG. 1 is a diagram illustrating the configuration of a first embodiment of the present invention.

A first embodiment of equipment for diagnosing the sliding condition of a rotating electrical machine in accordance with the present invention will now be described in detail with reference to FIGS. 1 and 2. FIG. 1 shows the configuration of the equipment for diagnosing the sliding condition of a rotating electrical machine in accordance with the first embodiment of the present invention.

In an electric sliding mechanism of the rotating electrical machine, which is shown in FIG. 1, one collecting brush 2 made of metal graphite comes into contact with the surface of a slip ring 1 made, for instance, of stainless steel. The slip ring 1 and the collecting brush 2 become energized and slide so that an electric current flows to the outside through a lead wire 3. While the electric sliding mechanism operates, a small discharge D intermittently occurs at an interface between the slip ring 1 and the collecting brush 2 due to electrical contact and separation therebetween. The small discharge D hardly occurs when the slip ring 1 and the collecting brush 2 slide in good contact with each other. However, when the contact between the slip ring 1 and the collecting brush 2 becomes unstable, the small discharge D frequently occurs to roughen the sliding surface S relative to the collecting brush 2. This results in an abnormal sliding condition in which the surface of the slip ring 1 is significantly roughened and the collecting brush 2 is abnormally worn.

The equipment for diagnosing the sliding condition in accordance with the present invention, which is provided for the electric sliding mechanism of the rotating electrical machine, includes a detection section 20 and a determination section 9. The detection section 20 includes a white light source 4, a filter 7, and a light-receiving section 5. The white light source 4 is a halogen lamp or other light source having a wide continuous spectrum and disposed near the sliding surface S of the slip ring 1, which is coated with the material (copper and graphite in the current example) of the collecting brush 2. The filter 7 transmits only light that is reflected from the sliding surface S and has a wavelength $\lambda_1$, for instance, of approximately 800 nm. The light-receiving section 5 converts the light transmitted through the filter 7 to electrical signal I. A signal having the wavelength $\lambda_1$ (800 nm) corresponds to a specific wavelength component.

An electrical signal I, which is derived from photoelectric conversion in the light-receiving section 5, is input to the determination section 9 through a signal line 6. The determination section 9 of the equipment for diagnosing the sliding condition in accordance with the present invention performs a process described below. The electrical signal intensity Io of transmitted light, which is acquired before an operation, is stored in the determination section 9. The light transmitted before the operation is obtained when light reflected from stainless steel, which is the material of the slip ring 1, is filtered by the filter 7. The electrical signal intensity Io can be regarded as a signal corresponding to the line (straight line) L1 that indicates the reflected light intensity of each wavelength of light reflected during normal sliding depicted in FIG. 7.

Signal intensity detection in the detection section 20 is periodically accomplished (at intervals of 1 or 24 hours) after the start of the operation to acquire prevailing transmitted light intensity I. The acquired transmitted light intensity I is input to the determination section 9 and successively compared with the transmitted light intensity Io prevailing before the operation. To perform this process, a gate 10 acquires the prevailing transmitted light intensity I on the periodic basis and permits a computation section 16 to successively compare the acquired transmitted light intensity I with the transmitted light intensity Io obtained before the operation, which is stored in a setting storage section 15.

If the result of the above comparison in the computation section 16 does not indicate that the difference between I and Io (I−Io) is greater than a predetermined threshold Ic (if the result is No), it is determined that a normal operation is being performed. If, on the other hand, the threshold Ic is exceeded (if the result is Yes), a sliding abnormality alarm is issued as copper is determined to be excessively attached to the sliding surface S. The threshold Ic varies, for instance, with the rotation speed of the rotating electrical machine and with the operating environment (temperature, humidity, and weather). Therefore, the threshold Ic for each set of such conditions should be databased and adjusted as appropriate in accordance with the conditions prevailing during measurement.

The chronological sequence of a process performed in the determination section 9 will now be described in detail with reference to FIG. 2. In FIG. 2, the horizontal axis represents a date and time before the operation and a plurality of dates and times after the operation, whereas the vertical axis represents the magnitude of a gate open/close signal, which is issued at regular intervals, and the magnitude of a transmitted light intensity signal I acquired in synchronism with the gate open/close signal. In this instance, for example, the gate 10 is opened at a predetermined time each day for a predetermined period of time (e.g., approximately 100 ms) to transmit an electrical signal indicative of transmitted light intensity.

The gate 10 is first opened at a predetermined time on January 1, which is before the operation of a power generator, and the intensity Io of transmitted light reflected from the slip ring 1, which is not coated, is measured and stored. The stored value is Io and used as an initial value. Subsequently, the gate 10 is opened at a predetermined time each day beginning with January 2 on which the operation is started, and the intensity I of transmitted light is measured each time the gate 10 is opened. If the difference between the initial value Io and the measured intensity I is not greater than the threshold Ic, the operation is continued as it is determined that normal sliding is in progress.

Subsequently, the same determination process as described above is repeated each day. In the example shown in FIG. 2, it is assumed that the intensity I of reflected transmitted light begins to increase on January 21 and exceeds the threshold Ic on January 23. When the threshold Ic is exceeded, the determination section 9 issues an alarm as it determines that abnormal sliding is in progress.

As described above, the present invention periodically performs a monitoring process to detect an increase in the intensity I of reflected transmitted light that occurs when constituent particles (the particles of copper in the current example) of the collecting brush 2 scatter and attach to the surface of the slip ring 1 due to the small discharge D. The fact that performing the above process contributes toward early detection of abnormal sliding will be described below.

Abnormal sliding occurs due, for instance, to unstable contact caused by a defective sliding part retainer or ambient environment degradation caused by improper humidity, improper temperature, or dust. Such unstable contact or environment degradation causes an arc discharge or other small discharge D so that the constituent particles (the particles of copper in the current example) of the collecting brush 2 scatter and excessively attach to the surface of the slip ring 1. Resulting surface irregularities cause the small discharge D to occur frequently. The above-mentioned sequence is then repeated to accelerate the occurrence of abnormal sliding (and abnormal wear of the collecting brush 2).

Consequently, it can be said that the small discharge D is a precursor phenomenon of abnormal sliding. As such being the case, when the filter 7 adapted to a wavelength related to high reflectivity of the attachment is used in accordance with the present embodiment to narrow down the range of wavelength of reflected light and monitor the intensity of such a wavelength region, abnormal sliding caused by the small discharge D can be detected early.

Further, a method of receiving light in accordance with the present invention need not be limited to the reception of specular reflected light. Therefore, the light source 4, the filter 7, and the light-receiving section 5 can be freely disposed near the sliding surface S as far as an adequate signal intensity is obtained.

It should be noted that the collecting brush 2 according to the present embodiment may be an electric graphite brush made of a silver-graphite alloy. When such an electric graphite brush is used as the collecting brush 2, silver excessively attaches to the surface of the slip ring 1. However, the silver has a high spectral reflectivity on a short-wavelength side (a wavelength of 300 to 400 nm) of visible light. Therefore, when, for instance, the filter 7 is changed to a filter that transmits only light having a wavelength $\lambda_1$ of approximately 400 nm, the above change in the material of the collecting brush 2 can be properly handled. In FIG. 7, the characteristics L3 represent characteristics obtained when silver is used.

Second Embodiment

Figure 3:
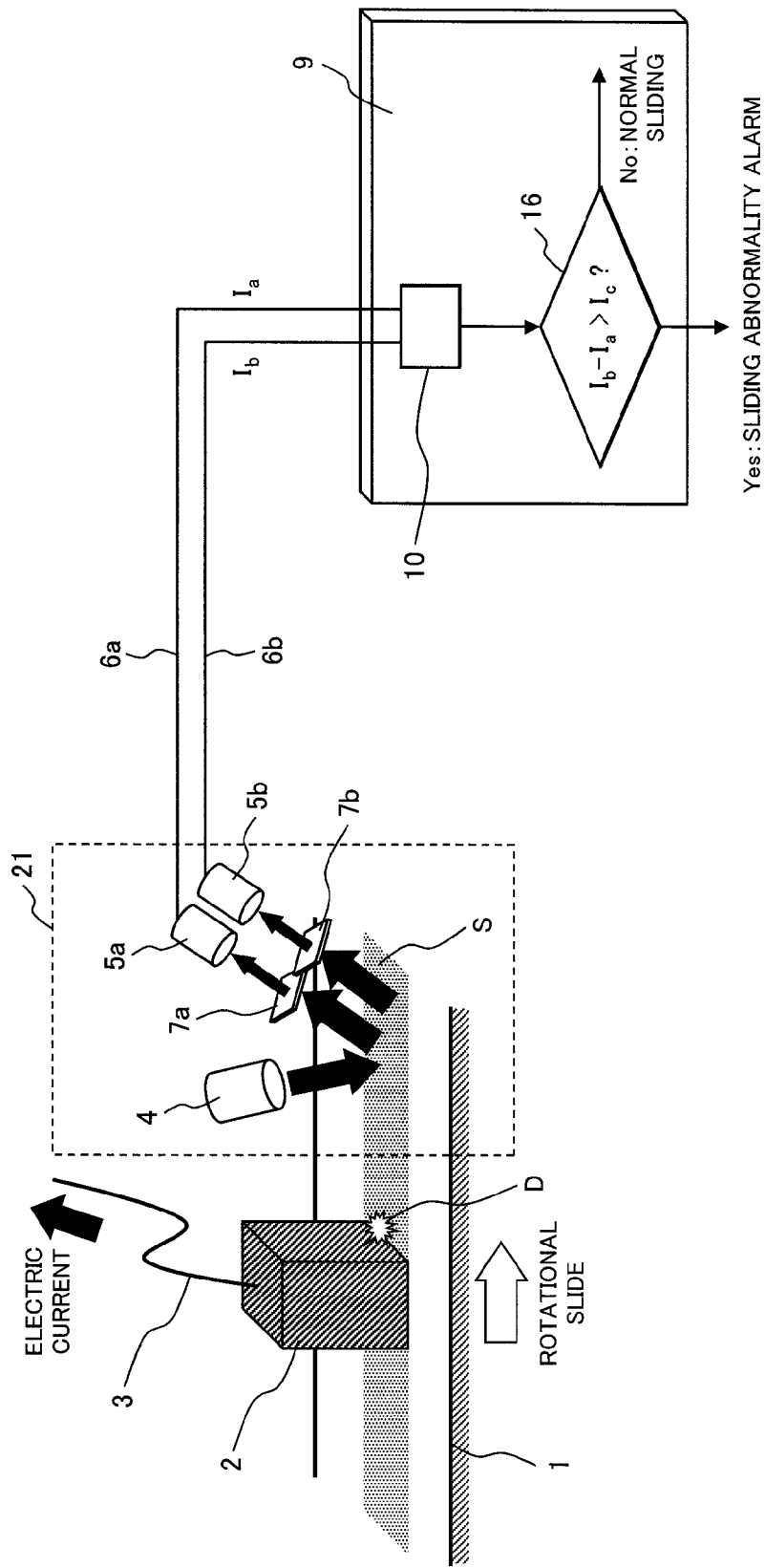
FIG. 3 is a diagram illustrating the configuration of a second embodiment of the present invention.
Figure 4:
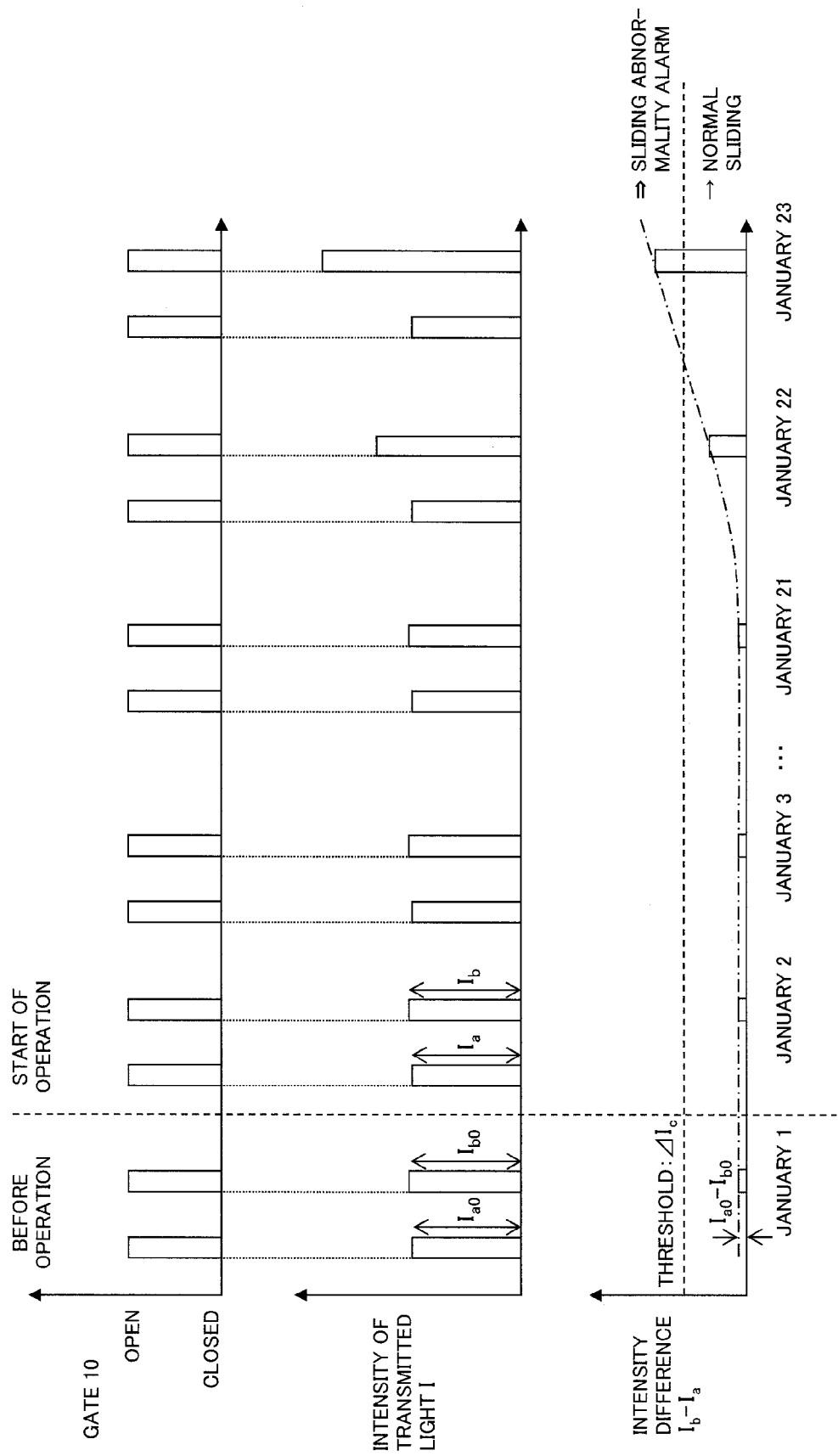
FIG. 4 is a diagram illustrating the chronological sequence of the internal process performed by the determination section 9 according to the second embodiment of the present invention.

A second embodiment of the equipment for diagnosing the sliding condition in accordance with the present invention will now be described in detail with reference to FIGS. 3 and 4. FIG. 3 shows the configuration of the second embodiment of the present invention. The electric sliding mechanism of the rotating electrical machine, which is included in the configuration shown in FIG. 3, is identical with the one shown in FIG. 1 and will not be redundantly described. A detection section 21 and subsequently disposed elements of the equipment for diagnosing the sliding condition will be described in detail.

The detection section 21 of the equipment for diagnosing the sliding condition in accordance with the second embodiment includes a white light source 4, a filter 7b, a filter 7a, a light-receiving section 5a, and a light-receiving section 5b. The white light source 4 is a halogen lamp or other light source having a wide continuous spectrum and disposed near the sliding surface S of the slip ring 1, which is coated with the material (copper and graphite in the current example) of the collecting brush 2. The filter 7b transmits only light that is reflected from the sliding surface S and has a wavelength $\lambda_1$, for instance, of approximately 800 nm. The filter 7a transmits only light that is reflected from the sliding surface S and has a wavelength $\lambda_2$, for instance, of approximately 400 nm. The light-receiving sections 5a, 5b convert the light transmitted through the filters 7a, 7b to electricity. A signal having the wavelength $\lambda_1$ (800 nm) corresponds to a specific wavelength component. A signal having the wavelength $\lambda_2$ (400 nm) corresponds to a non-specific wavelength component.

Electrical signals Ia, Ib, which are derived from photoelectric conversion in the light-receiving sections 5a, 5b, are input to a determination section 9 through signal lines 6a, 6b. The determination section 9 of the equipment for diagnosing the sliding condition in accordance with the present invention performs a process described below. Signal intensity detection in the detection section 21 is periodically accomplished (at intervals of 1 or 24 hours) after the start of the operation to acquire prevailing transmitted light intensities Ia, Ib from the filters 7a, 7b. The acquired transmitted light intensities Ia, Ib are input to the determination section 9 so that the difference between the transmitted light intensities Ia, Ib (Ib−Ia) are compared with a predetermined threshold ΔIc. To perform this process, a gate 10 periodically acquires the prevailing transmitted light intensities Ia, Ib and permits a computation section 16 to determine the difference (Ib−Ia) and compare the determined difference with the threshold ΔIc. If the difference (Ib−Ia) is not greater than the threshold ΔIc (if the result is No), it is determined that a normal operation is being performed. If, on the other hand, the threshold ΔIc is exceeded (if the result is Yes), a sliding abnormality alarm is issued as copper is determined to be excessively attached to the sliding surface S.

The chronological sequence of a process performed in the determination section 9 will now be described in detail with reference to FIG. 4. In FIG. 4, the horizontal axis represents a date and time before the operation and a plurality of dates and times after the operation, whereas the vertical axis represents the magnitude of a gate open/close signal, which is issued at regular intervals, and the magnitude of a transmitted light intensity signal I acquired by the gate open/close signal. In this instance, for example, the gate 10 is opened at a predetermined time each day for a predetermined period of time (e.g., approximately 100 ms) to transmit an electrical signal indicative of transmitted light intensity.

The gate 10 is opened for the predetermined period of time (e.g., approximately 100 ms) to transmit an electrical signal indicative of transmitted light intensity. At first, on January 1, which is before the operation of the power generator, the intensities Iao, Ibo of transmitted light reflected from the slip ring 1, which is not coated, are measured to verify the difference between the intensities Iao, Ibo (Iao−Ibo). This difference steadily arises between the reflected light intensity at the wavelength $\lambda_1$ (approximately 800 nm) and the reflected light intensity at the wavelength $\lambda_2$ (approximately 400 nm). A value sufficiently greater than the difference should be set as the threshold ΔIc.

Subsequently, the gate 10 is opened at a predetermined time each day beginning with January 2 on which the operation is started, and the transmitted light intensities Ia, Ib are measured each time the gate 10 is opened. The difference between the transmitted light intensities Ia, Ib (Ib−Ia) is then compared with the threshold ΔIc. If the difference (Ib−Ia) is not greater than the threshold ΔIc, the operation is continued as it is determined that normal sliding is in progress.

Subsequently, the same determination process as described above is repeated each day. In the example shown in FIG. 4, it is assumed that the difference (Ib−Ia) begins to increase on January 22 and exceeds the threshold ΔIc on January 23. When the threshold ΔIc is exceeded, the determination section 9 issues an alarm as it determines that abnormal sliding is in progress.

In the present embodiment, the difference between the intensity of reflected light having the wavelength $\lambda_1$ (approximately 800 nm) and the intensity of reflected light having the wavelength $\lambda_2$ (approximately 400 nm) is diagnosed as a factor. This difference also arises in a steady state and is a factor that will receive the influence of a phenomenon in which the intensity of reflected light having a wavelength of not less than the specific wavelength increases during abnormal sliding.

The difference between the intensities Iao, Ibo (Iao−Ibo) in the steady state varies with changes in ambient external light, which result, for instance, from changes in the weather and measurement time zone, or varies with changes in the light intensity of the light source 4. It is believed that the factor for such variation similarly affects the intensity of reflected light having the wavelength $\lambda_1$ (approximately 800 nm) and the intensity of reflected light having the wavelength $\lambda_2$ (approximately 400 nm). Therefore, even if the measured intensity of reflected light incident on the light-receiving sections 5a, 5b varies due to the above-mentioned factor, a more reliable diagnosis can be made of the sliding condition without being affected by such variation (as the influence of such variation is offset by determining the difference (Iao−Ibo)).

Further, the intensity of reflected light having the wavelength $\lambda_1$ (approximately 800 nm) is affected by a phenomenon in which the intensity of reflected light having a wavelength of not less than the specific wavelength increases during abnormal sliding. On the other hand, the intensity of reflected light having the wavelength $\lambda_2$ (approximately 400 nm) remains unaffected by such a phenomenon. Hence, an increase in the intensity of reflected light having the wavelength $\lambda_1$ (approximately 800 nm) is monitored while the intensity of reflected light having the wavelength $\lambda_2$ (approximately 400 nm) is used as a reference value. This makes it possible to achieve early detection of abnormal sliding.

If an electric graphite brush made of a silver-graphite alloy is adopted as is the case with the first embodiment, a diagnosis can be made by replacing the filter 7a with a filter that transmits light having a wavelength λ of 200 nm and replacing the filter 7b with a filter that transmits light having a wavelength λ of 400 nm.

Third Embodiment

Figure 5:
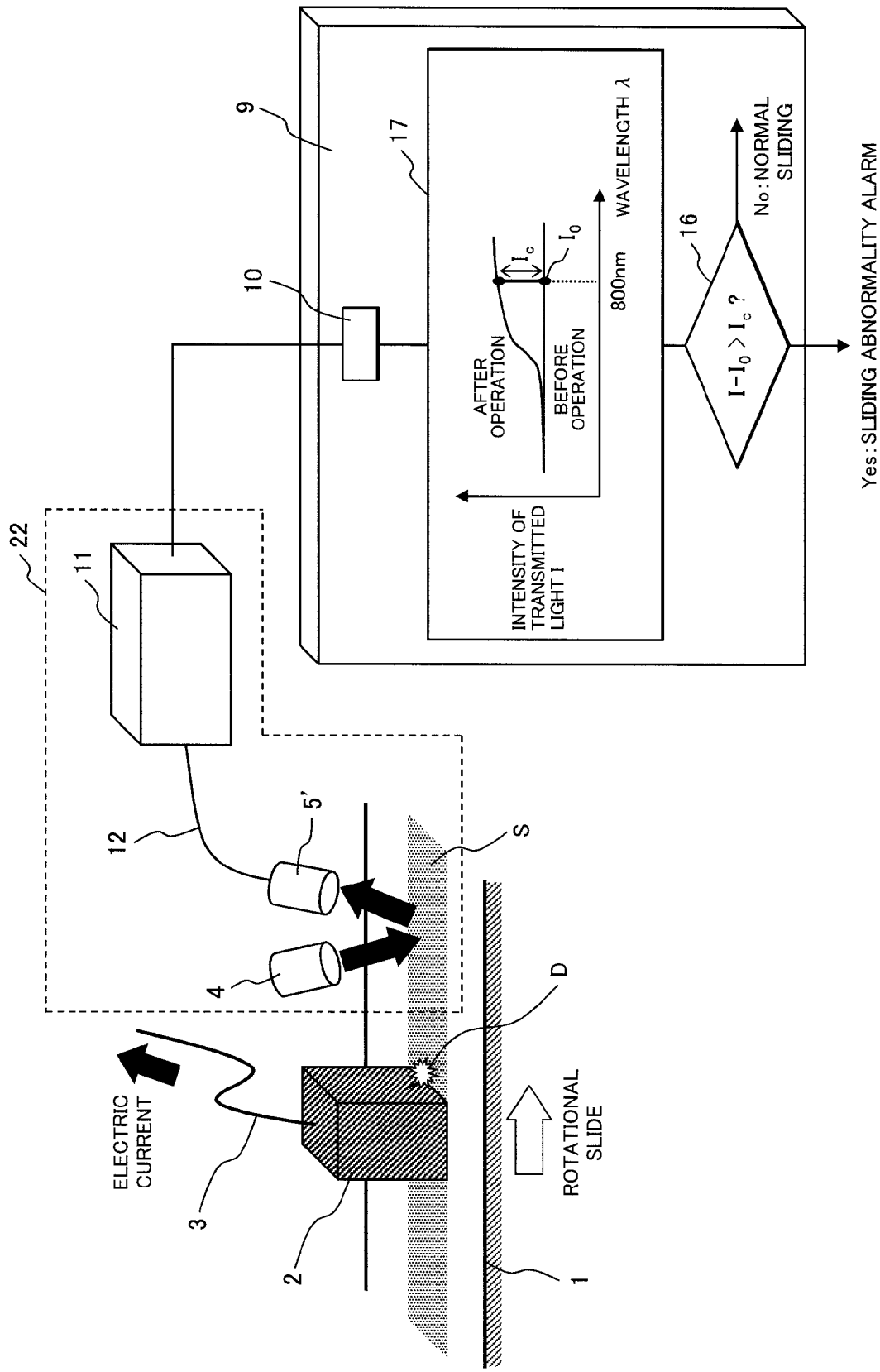
FIG. 5 is a diagram illustrating the configuration of a third embodiment of the present invention.

A third embodiment of the equipment for diagnosing the sliding condition in accordance with the present invention will now be described in detail with reference to FIG. 5. FIG. 5 shows the configuration of the third embodiment of the present invention.

In the third embodiment, which is shown in FIG. 5, the electric sliding mechanism of the rotating electrical machine also has the same configuration as the one shown, for instance, in FIG. 1. However, a detection section 22 and subsequently disposed elements of the equipment for diagnosing the sliding condition are different from the corresponding elements according to the other embodiments. The detection section 22 of the equipment for diagnosing the sliding condition according to the third embodiment receives the light reflected from the sliding surface S with a light-receiving section 5', which does not convert the light to electricity, and inputs the received light to a spectroscope 11 through an optical fiber 12.

The output of the spectroscope 11 is input to a determination section 9 and spectrally processed in an optical spectral processing section 17 in the determination section 9. The determination section 9 of the equipment for diagnosing the sliding condition in accordance with the present invention performs a process described below. First of all, an optical spectrum is obtained before an operation to store the intensity Io of light having a wavelength of 800 nm. After the operation is started, the intensity I of transmitted light is acquired at intervals of 1 or 24 hours and successively compared with transmitted light intensity Io prevailing before the operation.

If the result of the comparison made in a computation section 16 does not indicate that the difference between the intensity I and the intensity Io (I−Io) is greater than a threshold Ic (if the result is No), it is determined that a normal operation is in progress. If, on the other hand, the threshold Ic is exceeded (if the result is Yes), a sliding abnormality alarm is issued as copper is determined to be excessively attached to the sliding surface S. The threshold Ic varies, for instance, with the rotation speed of the rotating electrical machine and with the operating environment (temperature, humidity, and weather). Therefore, the threshold Ic for each set of such conditions should be databased and adjusted as appropriate in accordance with the conditions prevailing during measurement.

Figure 2:
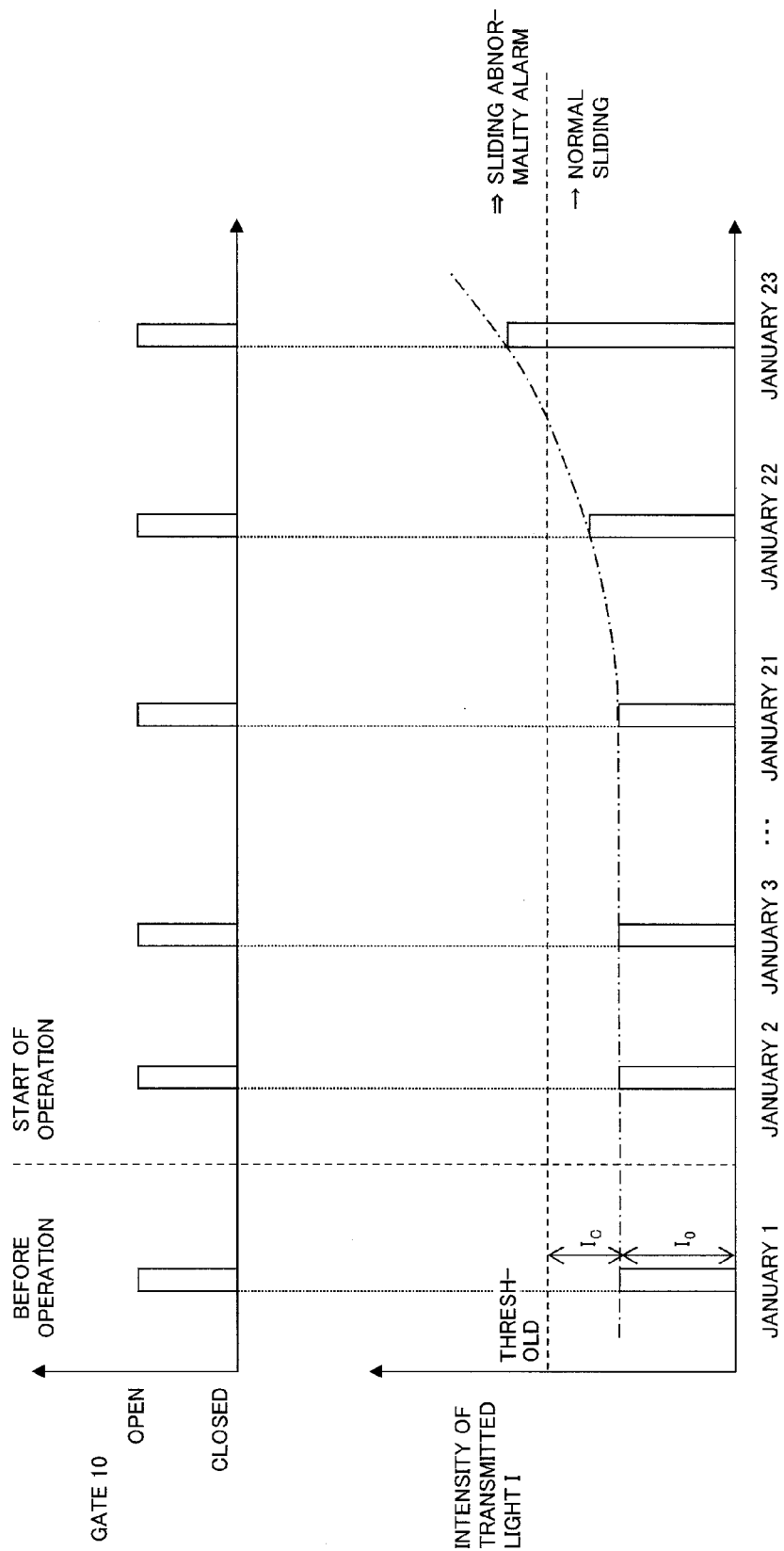
FIG. 2 is a diagram illustrating the chronological sequence of an internal process performed by a determination section according to the first embodiment of the present invention.

To implement the above-described functionality, the determination section 9 internally performs the same process as indicated in the chronological diagram of FIG. 2 to open the gate 10 for a predetermined period of time (e.g., approximately 100 ms), and acquires optical spectrum data from an uncoated slip ring 1 and the intensity Io of reflected light having a wavelength of 800 nm on January 1, which is before the operation of the generator.

The intensity I of transmitted light is measured at a predetermined time each day beginning with January 2 on which the operation is started. If the difference between the intensity I and the intensity Io is not greater than the threshold Ic, the operation is continued as it is determined that normal sliding is in progress. Subsequently, when the intensity I begins to increase on January 21 and exceeds the threshold Ic on January 23, the determination section 9 issues an alarm as it determines that abnormal sliding is in progress.

Even if the characteristics of light reflected from the sliding surface S are changed due to the above-described change in the material of the collecting brush 2 in a situation where the spectroscope 11 is used in place of the filter 7 as is the case with the present embodiment, the change in the material of the collecting brush 2 can be easily coped with simply by adjusting a software setting to change the wavelength λ to be extracted from the optical spectrum acquired in the determination section 9. Further, when, for instance, wavelengths of 750 nm and 850 nm, which are close to a selected wavelength of 800 nm, are simultaneously subjected to comparison, an erroneous diagnosis can be avoided to further increase the reliability of diagnosis.

Fourth Embodiment

Figure 6:
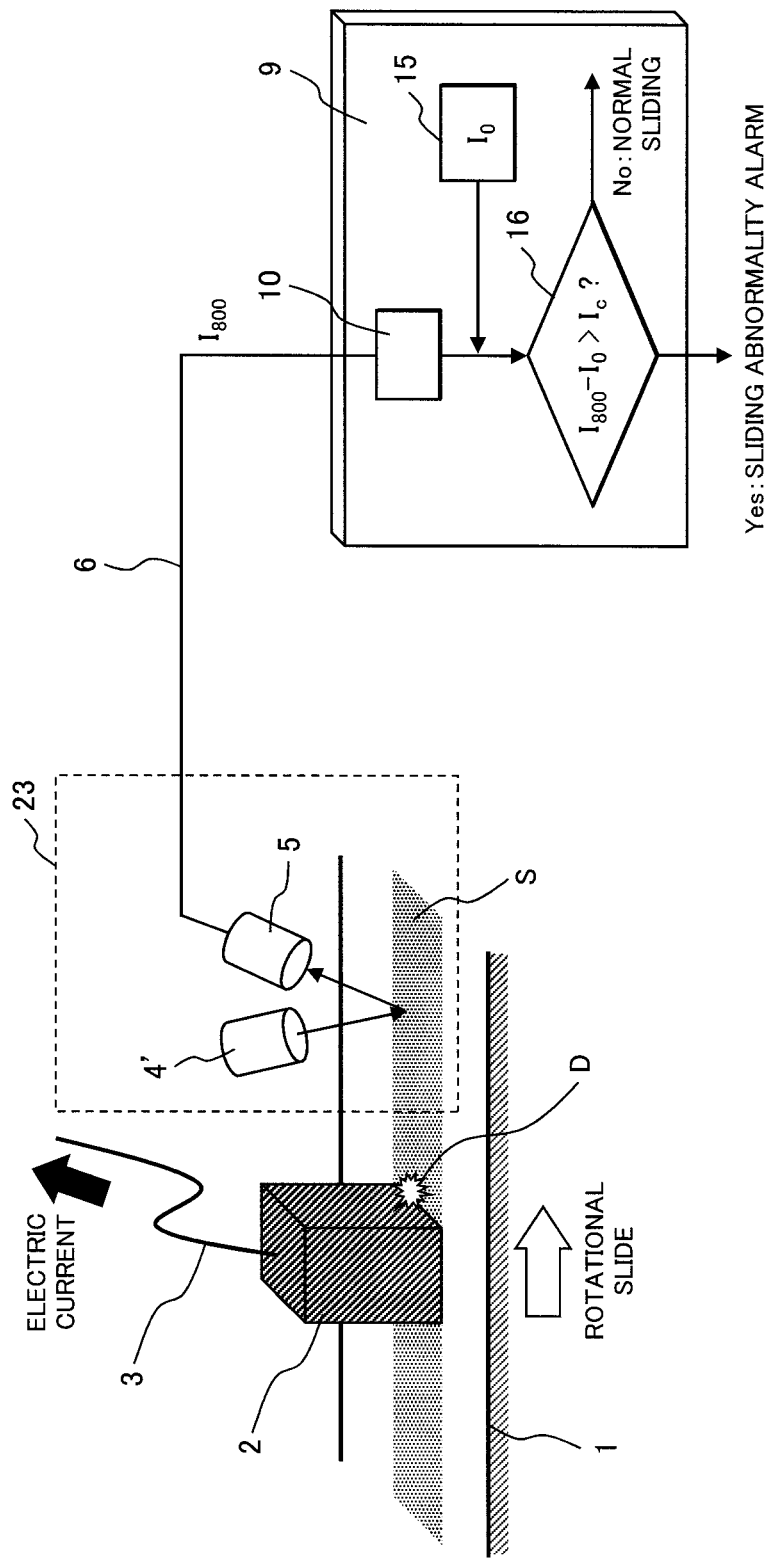
FIG. 6 is a diagram illustrating the configuration of a fourth embodiment of the present invention.

A fourth embodiment of the equipment for diagnosing the sliding condition in accordance with the present invention will now be described in detail with reference to FIG. 6. FIG. 6 shows the configuration of the equipment for diagnosing the sliding condition of a rotating electrical machine in accordance with the fourth embodiment of the present invention.

In the present embodiment, a detection section 23 of the equipment for diagnosing the sliding condition includes, for example, a monochromatic light source 4' having a wavelength λ of 800 nm in place of a white light source. This eliminates the necessity of disposing the filter 7 before the light-receiving section 5. The intended purpose is achieved by performing a process of comparing the signal intensity $I_{800}$ at a wavelength λ of 800 nm with the intensity Io. Thus, the present embodiment can make a diagnosis with an extremely simple configuration as compared to the other embodiments.

What is claimed is:

1. Equipment for diagnosing a sliding condition of a rotating electrical machine, the equipment comprising:
    a light source that emits light onto a sliding surface of a collecting brush relative to a surface of a rotating body of the rotating electrical machine;
    a light-receiving section that receives light reflected from the sliding surface; and
    a determination section that processes a signal from the light-receiving section;
    wherein the determination section is arranged to compare a specific wavelength component of the reflected light with a non-specific wavelength component of the reflected light, the non-specific wavelength component being a wavelength component other than the specific wavelength component, and to detect an increase in a difference between the compared wavelength components to determine whether the sliding condition of the rotating electrical machine is abnormal.

2. The equipment according to claim 1, further comprising a filter that transmits the specific wavelength component of the reflected light, wherein the light-receiving section receives light reflected from the sliding surface through the filter.

3. The equipment according to claim 1, wherein the determination section is arranged to determine the specific wavelength component of the reflected light by performing optical spectral processing.

4. The equipment according to claim 1, wherein the light source is a monochromatic light source having the specific wavelength component.

5. The equipment according to claim 1, wherein the specific wavelength component of the reflected light is 600 nm or more.

6. The equipment according to claim 1, wherein the specific wavelength component of the reflected light of is 300 nm or more.

7. A method for diagnosing a sliding condition of a rotating electrical machine that uses light incident on and reflected from a sliding surface of a collecting brush relative to a surface of a rotating body of the rotating electrical machine, the method comprising the steps of:
    comparing a specific wavelength component of the light reflected from the sliding surface with a non-specific wavelength component of the reflected light, the non-specific wavelength component being a wavelength component other than the specific wavelength component, and
    detecting an increase in a difference between the compared wavelength components to determine whether the sliding condition of the rotating electrical machine is abnormal.

8. The method according to claim 7, wherein the specific wavelength component of the reflected light is 600 nm or more.

9. The method according to claim 7, wherein the specific wavelength component of the reflected light is 300 nm or more.

\* \* \* \* \*